United States Patent
Tanedani

(10) Patent No.: US 8,790,676 B2
(45) Date of Patent: Jul. 29, 2014

(54) MICROENCAPSULATED PESTICIDE

(75) Inventor: Toshiyuki Tanedani, Nishitokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1102 days.

(21) Appl. No.: 12/086,340

(22) PCT Filed: Nov. 21, 2006

(86) PCT No.: PCT/JP2006/323629
§ 371 (c)(1),
(2), (4) Date: Jun. 11, 2008

(87) PCT Pub. No.: WO2007/069448
PCT Pub. Date: Jun. 21, 2007

(65) Prior Publication Data
US 2009/0162409 A1    Jun. 25, 2009

(30) Foreign Application Priority Data

Dec. 12, 2005  (JP) .................................. 2005-357296

(51) Int. Cl.
*A01N 25/28* (2006.01)
*A01N 37/18* (2006.01)
*A01N 43/40* (2006.01)
*A01N 43/38* (2006.01)

(52) U.S. Cl.
USPC ............ 424/408; 514/365; 514/357; 514/421

(58) Field of Classification Search
None
See application file for complete search history.

(56) References Cited

U.S. PATENT DOCUMENTS

| 4,309,213 A | | 1/1982 | Graber et al. | |
| 4,900,551 A | * | 2/1990 | Ohtsubo et al. | 424/408 |
| 4,933,371 A | * | 6/1990 | Hink et al. | 514/739 |
| 5,693,344 A | * | 12/1997 | Knight et al. | 424/687 |
| 5,773,030 A | * | 6/1998 | Nastke et al. | 424/490 |
| 6,015,571 A | | 1/2000 | Scher et al. | |
| 2002/0086044 A1 | * | 7/2002 | Voris et al. | 424/406 |
| 2003/0153464 A1 | * | 8/2003 | Nakamura et al. | 504/257 |
| 2006/0057173 A1 | * | 3/2006 | Sims | 424/405 |

FOREIGN PATENT DOCUMENTS

| JP | 54-135671 | 10/1979 | |
| JP | 5-201814 | 8/1993 | |
| JP | 6-256116 | 9/1994 | |
| JP | 7-48530 | 2/1995 | |
| JP | 7-112902 | 5/1995 | |
| JP | 8-99805 | 4/1996 | |
| JP | 10-287510 | 10/1998 | |
| JP | 2004-99536 | 4/2004 | |
| JP | 2005-528200 | 9/2005 | |
| WO | WO 0027197 A1 * | 5/2000 | |
| WO | WO 02/089578 A1 | 11/2002 | |
| WO | WO03051116 A1 * | 6/2003 | A01N 25/28 |
| WO | WO-03/101606 A1 | 12/2003 | |
| WO | WO 2004/016234 A1 | 2/2004 | |

OTHER PUBLICATIONS

Notice of Grounds of Rejection in JP Appln No. 2006-321453 dated Dec. 27, 2011.

* cited by examiner

*Primary Examiner* — Kyle Purdy

(74) *Attorney, Agent, or Firm* — Foley & Lardner LLP

(57) ABSTRACT

A microcapsule can be produced readily by (a) pulverizing a solid pesticidal compound in terpineol, dihydroterpineol, terpinel acetate, dihydroterpinel acetate or a mixture thereof to form a suspension, (b) mixing the resulting suspension and water to prepare a liquid droplet, and (c) forming a coating film of a resin around the liquid droplet. The microcapsule obtained by such a method contains most of the solid pesticidal compound within the microcapsule.

10 Claims, No Drawings

MICROENCAPSULATED PESTICIDE

TECHNICAL FIELD

The present invention relates to microcapsules of pesticidal compounds.

BACKGROUND ART

Conventionally, microcapsule formulations are known as sustained-release formulations of pesticidal compounds. Several methods are known as techniques of microencapsulating pesticidal compounds. An interfacial polymerization method is used favorably because it is easy to control the coating film thickness of microcapsules and therefore it is easy to adjust the sustained-release performance of pesticidal compounds appropriately. Microencapsulation by the interfacial polymerization method is disclosed, for example, in Japanese Patent Laid-Open Nos. 5-201814 and 8-99805.

Usually, in the event that a water-insoluble pesticidal compound can be dissolved in a water-insoluble organic solvent, it is possible to obtain microcapsules by dispersing a solution of the pesticidal compound in the organic solvent to form liquid droplets in water and forming a coating film of a resin by polymerization at the interfaces between the liquid droplets and water. In the case of a highly water-soluble pesticidal compound, however, it is difficult to make the pesticidal compound be enclosed sufficiently in microcapsules by such interfacial polymerization or in-situ polymerization because the pesticidal compound adversely dissolves in water.

DISCLOSURE OF THE INVENTION

The present invention provides a method for producing a microcapsule containing therein a pesticidal compound and a microcapsule which can be applied even to highly water-soluble pesticidal compounds.

The present invention provides a microcapsule wherein a liquid droplet in which a solid pesticidal compound is suspended in terpineol, dihydroterpineol, terpinel acetate, dihydroterpinel acetate or a mixture thereof is coated with a resin, and a method for producing a microcapsule including (a) pulverizing a solid pesticidal compound in terpineol, dihydroterpineol, terpinel acetate, dihydroterpinel acetate or a mixture thereof to form a suspension, (b) mixing the resulting suspension and water to prepare a liquid droplet, and (c) forming a coating film of a resin around the liquid droplet.

The solid pesticidal compound in the present invention is a pesticidally active compound which usually has a melting point of 15° C. or higher, and preferably has a melting point of 50° C. or higher. Preferred is a compound having a solubility to any of terpineol, dihydroterpineol, terpinel acetate and dihydroterpinel acetate of 5% or less.

Examples of solid pesticidal compounds which can be used for the present invention include insecticidal compounds, fungicidal compounds, herbicidal compounds, insect growth-regulating compounds, plant growth-regulating compounds, and insect repellent compounds. Specific examples are compounds shown below.

Examples of the insecticidal compound include carbamate compounds such as propoxur, isoprocarb, xylylcarb, metolcarb, XMC, carbaryl, pyrimicarb, carbofuran, methomyl, phenoxycarb, alanycarb and metoxadiazone; organophosphorus compounds such as acephate, phenthoate, vamidothion, trichlorfon, monocrotophos, tetrachlorvinphos, dimethylvinphos, phosalone, chlorpyrifos, chlorpyrifos-methyl, pyridafenthion, quinalphos, methidathion, methamidophos, dimethoate, formothion, azinphos-ethyl, azinphos-methyl and salithion; neonicotinoid compounds such as imidacloprid, nitenpyram, acetamiprid, clothianidin and thiamethoxam; 4-chloro-2-(2-chloro-2-methylpropyl)-5-(6-iodo-3-pyridylmethoxy)pyridazin-3(2H)-one, cartap, buprofezin, thiocyclam, bensultap, phenoxycarb, fenazaquin, fenpyroximate, pyridaben, hydramethylnon, thiodicarb, chlorfenapyr, fenproxymate, pymetrozine, pyrimidifen, tebufenozide, tebufenpyrad, triazamate, indoxacarb, sulfluramid, milbemectin, avermectin and p-dichlorobenzene.

Examples of the fungicidal compound include benzimidazole compounds such as benomyl, carbendazim, thiabendazol and thiophanate-methyl; phenyl carbamate compounds such as diethofencarb; dicarboxylmide compounds such as procymidone, iprodione and vinclozolin; azole compounds such as diniconazole, probenazole, epoxyconazole, tebuconazole, difenoconazole, cyproconazole, flusilazole and triadimefon; acylalanine compounds such as metalaxyl; carboxamide compounds such as furametpyr, mepronil, flutolanil and trifluzamide; organophosphorus compounds such as triclofos-methyl, fosetyl-aluminum and pyrazophos; anilinopyrimidine compounds such as pyrimethanil, mepanipyrim and cyprodinil; cyanopyrrole compounds such as fludioxonil and fenpiclonil; chlorothalonil, mancozeb, captan, folpet, tricyclazole, pyroquilon, probenazole, fthalide, cymoxanil, dimethomorph, famoxadone, oxolinic acid and its salts, fluazinam, ferimzone, diclocymet, chlobenthiazone, isovaledione, tetrachloroisophth alonitrile, thiophthalimideoxybisphenoxyarsine and 3-iodo-2-propyl butyl carbamate.

Examples of the herbicidal compound include triazine compounds such as atrazine and metribuzin; urea compounds such as fluometuron and isoproturon; hydroxybenzonitrile compounds such as bromoxynil and ioxynil; 2,6-dinitroaniline compounds such as pendimethaline and trifluralin; aryloxyalkanoic acid compounds such as 2,4-D, dicamba, fluoroxypyr and mecoprop, and salts thereof; sulfonylurea compounds such as bensulfuron-methyl, metsulfuron-methyl, nicosulfuron, primisulfuron-methyl and cyclosulfamuron; imidazolinone compounds such as imazapyr, imazaquin and imazethapyr, and salts thereof; sulfentrazone, paraquat, flumeturam, triflusulfron-methyl, fenoxaprop-p-ethyl, cyhalofop-butyl, diflufenican, norflurazone, isoxaflutole, ammonium salt of glufosinate, glyphosate salts, bentazone, benthiocarb, mefenacet, propanil, fluthiamide, flumiclorac-pentyl and flumioxazine.

Examples of the insect growth-regulating compound include benzoylurea compounds such as diflubenzuron, chlorofluazuron, lufenuron, hexaflumuron, flufenoxuron, flucycloxuron, cyromazine, diafenthiuron, hexythiazox, novaluron, teflubenzuron, triflumuron, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea and 1-(2,6-difluorobenzoyl)-3-[2-fluoro-4-(1,1,2,2-tetrafluoroethoxy)phenyl]urea; and pyriproxyfen. Examples of the plant growth-regulating compounds include maleic hydrazide, chlormequat, ethephon, gibberellin, mepiquat chloride, thidiazuron, inabenfide, paclobutrazole and uniconazole. Examples of the insect repellent compound include 1S,3R,4R,6R-carane-3,4-diol and dipropyl 2,5-pyridinedicarboxylate.

According to the present invention, any pesticidal compound capable of being suspended in terpineol, dihydroterpineol, terpinel acetate, dihydroterpinel acetate or a mixture thereof to be dispersed in the form of solid particles can be microencapsulated even if it, for example, has a solubility in water as high as 100 mg/L or more in terms of the water-solubility at 20° C.

Terpineol is a compound which is contained in plant essential oils such as linaloe oil, petitgrain oil, cypress oil, camphor oil and lemon oil and which is represented by a compositional formula $C_{10}H_{18}O$. It can be produced by fractional distillation of such plant essential oils or by dehydration using dilute sulfuric acid of terpin hydrate, which is obtained by hydrolysis of pinene using sulfuric acid. While terpineol has isomers such as α-terpineol, β-terpineol and γ-terpineol, any terpineol can be employed. Products which are usually commercially available are mixtures of α-terpineol, β-terpineol and γ-terpineol which mainly contain α-terpineol. Such commercially available products can be used as received.

Dihydroterpineol is a compound represented by a compositional formula $C_{10}H_{20}O$ resulting from addition of one molecule of hydrogen atoms to the double bond in the aforesaid terpineol and it can be produced by hydrogenating terpineol. Like terpineol, dihydroterpineol is usually available in the market as mixtures of isomers which mainly contain dihydro-α-terpineol. Such commercially available products can be used as received.

Terpinel acetate is a compound represented by a compositional formula $C_{12}H_{20}O_2$ resulting from acetylation of a hydroxyl group in the molecule of terpineol and it can be produced by causing terpineol and acetic anhydride to react in the presence of phosphoric acid. Products which are usually commercially available are mixtures of α-terpinel acetate, β-terpinel acetate and γ-terpinel acetate which mainly contain α-terpinel acetate. Such commercially available products can be used as received.

Dihydroterpinel acetate is a compound represented by a compositional formula $C_{12}H_{22}O_2$ resulting from addition of one molecule of hydrogen atoms to the double bond in terpinel acetate and it can be produced by hydrogenating terpinel acetate or acetylating dihydroterpineol. Like terpinel acetate, products which are commercially available are mixtures of isomers which mainly contain dihydro-α-terpinel acetate. Such commercially available products can be used as received. Dihydro-α-terpinel acetate is a compound which generally is also called p-menthan-8-yl acetate.

The structures of α-terpineol, dihydro-α-terpineol, α-terpinel acetate and dihydro-α-terpinel acetate are illustrated below.

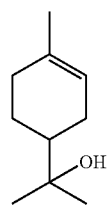
α-Terpineol

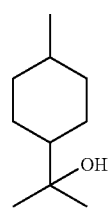
Dihydro-α-terpineol

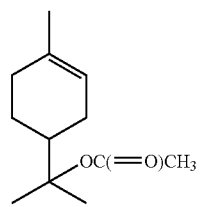
α-terpinel acetate

-continued

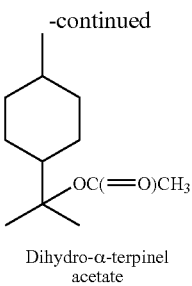
Dihydro-α-terpinel acetate

In the microcapsule of the present invention, the liquid droplet in the microcapsule is a material in which the solid pesticidal compound is suspended in terpineol, dihydroterpineol, terpinel acetate, dihydroterpinel acetate or a mixture thereof. It may further contain another organic solvent. Examples of the organic solvent include aliphatic hydrocarbons such as trimethylpentane, aromatic hydrocarbons such as phenylxylylethane, alkylbenzene and alkylnaphthalene, ethers such as 2-ethyl hexyl ether, mineral oils such as machining oil, and vegetable oils such as cottonseed oil. The amount of the organic solvent is usually ½ or less, preferably ⅜ or less, and more preferably ¼ or less in weight ratio based on the amount of terpineol, dihydroterpineol, terpinel acetate, dihydroterpinel acetate or a mixture thereof. The amount of the solid pesticidal compound in the liquid droplet is usually from 5/100 to 40/100, and preferably from 10/100 to 30/100 in weight ratio based on the amount of terpineol, dihydroterpineol, terpinel acetate, dihydroterpinel acetate or a mixture thereof.

In the present invention, the particle diameter of the solid pesticidal compound particles suspended in the liquid droplet is usually 10 μm or less, and preferably within the range of from 1 to 5 μm in volume median diameter. It is preferable that the cumulative volume of the particles having a particle diameter of not less than 10 μm is 10% or less.

The volume median diameter (VMD) is a value such that the sum total of the volumes of particles smaller than the value and the sum total of the volumes of particles larger than that value each account for 50% of the sum total of the volumes of all the particles. The volume median diameter is calculated by analyzing images of many particles measured by a laser beam diffraction scattering method based on the Mie scattering theory. One specific example of the instrument for the measurement thereof is Mastersizer 2000 (the name of a product manufactured by Malvern Instruments Ltd.).

In the present invention, the particle diameter of the liquid droplet in a microcapsule is almost equal to that of the microcapsule. The particle diameter of a microcapsule is usually within the range of from 1 to 80 μm, and preferably within the range of from 5 to 50 μm in volume median diameter.

In the present invention, examples of the resin to form the coating film of a microcapsule include a polyurethane resin, a polyurea resin, a polyamide resin, a polyester resin, a polysulfonate resin, a polysulfonamide resin, an aminoplast resin, a urea-formalin resin, and a melamine-formalin resin. In particular, use of a polyurethane resin or a polyurea resin, which affords a microcapsule with good storage stability, especially good storage stability at high temperatures, is preferred.

In the present invention, the amount of the resin forming the coating film of a microcapsule is usually within the range of from 5 to 30% by weight based on the overall amount of the microcapsule.

The coating of a liquid droplet with a resin is performed usually by forming a coating film of the resin by an interfacial polymerization method. The coating film can be formed by, while having dissolved, in a pesticidal compound suspension, an oil-soluble raw material out of the two raw materials for forming the resin and having dissolved, in water in which the suspension is to be dispersed, a water-soluble raw material out of the two raw materials for forming the resin, performing a polymerization reaction between the two raw materials at the interface between a suspension droplet and the water. The thickness of the coating film can be calculated from the particle diameter of the liquid droplet and the amount of the resin to form the coating film.

The polyurethane resin or the polyurea resin to be used as the coating film of the microcapsule of the present invention is usually obtained by causing a polyisocyanate to react with a polyalcohol or a polyamine.

Examples of the polyisocyanate include hexamethylene diisocyanate, a hexamethylene diisocyanate-trimethylolpropane adduct, a biuret condensate of three hexamethylene diisocyanate molecules, a tolylene diisocyanate-trimethylolpropane adduct, an isocyanurate condensate of tolylene diisocyanate, an isocyanurate condensate of hexamethylene diisocyanate, an isocyanurate condensate of isophorone diisocyanate, an isocyanate prepolymer in which one isocyanate moiety of hexamethylene diisocyanate constitutes an isocyanurate form together with two tolylene diisocyanate molecules and the other isocyanate moiety constitutes an isocyanurate form together with two other hexamethylene diisocyanate molecules, 4,4'-methylenebis(cyclohexylisocyanate), and trimethylhexamethylene diisocyanate. Use of a tolylene diisocyanate-trimethylolpropane adduct, an isocyanurate condensate of tolylene diisocyanate, an isocyanurate condensate of hexamethylene diisocyanate, or an isocyanurate condensate of isophorone diisocyanate is preferred.

Examples of the polyalcohol include ethylene glycol, propylene glycol, butylene glycol and cyclopropylene glycol. Examples of the polyamine include ethylenediamine, hexamethylenediamine, diethylenetriamine and triethylenetetramine.

The microcapsule of the present invention is generally used as a pesticidal composition in the form of an aqueous suspension composition wherein it is dispersed in water. The pesticidal composition contains the microcapsule dispersed in water, and it may further contain an additive, such as a thickener, an antifreezing agent, a preservative or a specific gravity regulator, which is added according to necessity. The weight of water in the pesticidal composition is usually from 0.8 to 2 times the weight of the microcapsule.

Next, a method for producing the microcapsule of the present invention is described.

The production method comprises a first step of (a) pulverizing a solid pesticidal compound in terpineol, dihydroterpineol, terpinel acetate, dihydroterpinel acetate or a mixture thereof to form a suspension, a second step of (b) mixing the resulting suspension and water to prepare a liquid droplet, and a third step of (c) forming a coating film of a resin around the liquid droplet.

In the first step, the pulverization of the solid pesticidal compound is performed by use of a pulverizer such as a bead mill, a ball mill or a rod mill. Specific examples of the pulverizer include Attritor (manufactured by Mitsui Miike Kakoki), DYNO-MILL (manufactured by WILLY A. BACHOFEN AG. MASHINENFABRIK, Switzerland), Colloid Mill (manufactured by Tokushu Kika Kogyo Co., Ltd.), and Pearl Mill (manufactured by Ashizawa Iron Works Co., Ltd.). A solid pesticidal compound, as well as beads for pulverization or the like to be added according to necessity, is added to terpineol, dihydroterpineol, terpinel acetate, dihydroterpinel acetate or a mixture thereof, and pulverization is performed using a pulverizer. If a solid pesticidal compound is wet-pulverized in the presence of terpineol, dihydroterpineol, terpinel acetate, dihydroterpinel acetate or a mixture thereof, a power load on a pulverizer in the first step is low and the production is easy because particles of the solid pesticidal compound are dispersed uniformly and also because particles after pulverization hardly flocculate and the viscosity of the suspension in the wet pulverization does not become so high.

In the event that the resin to form the coating film is a polyurethane resin or a polyurea resin, a polyisocyanate is added to the suspension obtained in the first step beforehand.

It is preferable that the suspension obtained in the first step be used promptly in the next step.

In the second step, a stirrer such as a propeller stirrer, a turbine stirrer or a high-speed shear stirrer is used in order to mix the suspension and water to prepare a liquid droplet. Specific examples of the stirrer include T. K. Homomixer (manufactured by Tokushu Kika Kogyo Co., Ltd.), CLEARMIX (manufactured by M Technique Co., Ltd.), POLYTRON homogenizer and MEGATRON homogenizer (manufactured by KINEMATICA AG), and Supraton (manufactured by Tsukishima Kikai Co., Ltd.). The suspension is added to water, followed by stirring with a stirrer.

The weight of the water into which the suspension is to be dispersed is usually within the range of from 0.8 to 2 times the weight of the suspension. As the water into which the suspension is to be dispersed, deionized water is preferably used and an additive, such as a thickener, an antifreezing agent, a preservative or a specific gravity regulator, may be added thereto according to necessity.

Examples of the thickener include natural polysaccharides, such as xanthan gum, rhamsan gum, locust bean gum, carrageenan and werant gum, synthetic polymers such as sodium polyacrylate, semisynthetic polymers such as carboxymethylcellulose, mineral powders such as aluminum magnesium silicate, smectite, bentonite, hectorite and dry silica, and alumina sol. The antifreezing agent may be propylene glycol, or the like. Examples of the preservative include p-hydroxybenzoic acid esters and salicylic acid derivatives. Examples of the specific gravity regulator include water-soluble salts such as sodium sulfate and water-soluble compounds such as urea.

The suspension is low in viscosity and when it is mixed with water using a stirrer, it is dispersed in water relatively easily to form a liquid droplet. Because strong agitation is not required in dispersing, there are not so many limitations with the equipment for practicing this step. Even in the use of a solid pesticidal compound which is high in solubility in water, the solid pesticidal compound is retained as solid particles in terpineol, dihydroterpineol, terpinel acetate, dihydroterpinel acetate or a mixture thereof, and therefore a liquid droplet can be prepared with almost no transfer of the solid pesticidal compound into an aqueous phase.

In the event that the resin to form the coating film is a polyurethane resin, a polyalcohol is added beforehand to the water in which the suspension is to be dispersed, or a polyalcohol is added to an aqueous phase after the second step. In the event that the resin to form the coating film is a polyurea resin, an acid addition salt of a polyamine is added beforehand to the water in which the suspension is to be dispersed, or an acid addition salt of a polyamine, such as a hydrochloric acid salt or an acetic acid salt, is added after the second step.

It is preferable that an aqueous dispersion of the liquid droplet in water obtained in the second step be used promptly in the next step.

In the third step, the method for forming the coating film of a resin around the liquid droplet is not particularly restricted and usual microencapsulation methods, such as an interfacial polymerization method and an in-situ polymerization method, can be employed. The interfacial polymerization method is performed, for example, by heating an aqueous dispersion of a liquid droplet containing raw materials added beforehand to a temperature at which a polymerization reaction can proceed, or by adding one raw material for forming the resin into the aqueous phase of the aqueous dispersion of the liquid droplet, or by activating one raw material for forming the resin by pH adjustment, or the like.

In the event that the resin to form the coating film is a polyurethane resin, a coating film of the polyurethane resin is formed around a liquid droplet, for example, by heating an aqueous dispersion of the liquid droplet to 40 to 80° C. under stirring and holding it for about 0.5 to 48 hours. In the event that the resin to form the coating film is a polyurea resin, a coating film of the polyurea resin is formed around a liquid droplet, for example, by adjusting the liquid property of an aqueous dispersion of the liquid droplet to be neutral to weakly alkaline and holding it at 0 to 50° C. for about 0.5 to 48 hours.

In an aqueous suspension composition of a microcapsule obtained in such a way, almost all the solid pesticidal compound is present as solid particles within the microcapsule and the amount of the pesticidal compound dissolved or suspended in water which is present outside the coating film of the microcapsule is smaller in comparison to the entire amount of the pesticidal compound.

An aqueous suspension composition of a microcapsule of the present invention obtained by the production method described above can be used also as a powdery microcapsule formulation by centrifugal separation, filtration, spray drying, or the like. Moreover, the aqueous suspension composition of the microcapsule can also be used after addition of a thickener, an antifreezing agent, a preservative, a specific gravity regulator, water, or the like.

The microcapsule of the present invention is used, for example, as a pesticidal composition containing a solid pesticidal compound in an amount of from 0.1 to 30% by weight in the entire amount of an aqueous suspension composition.

In the event that the solid pesticidal compound is an insecticidally effective component, a pesticidal composition containing the microcapsule of the present invention is administered by spraying it to injurious insects or a habitat thereof at a rate of from about 0.1 to about 1000 g/1000 m$^2$, and preferably from about 1 to about 100 g/1000 m$^2$ in the amount of the solid pesticidal compound.

EXAMPLES

The present invention is described in more detail below by way of production examples and test examples, but the invention is not limited to the examples.

Nitempyram ((E)-N-(6-chloro-3-pyridylmethyl)-N-ethyl-N'-methyl-2-nitrovinylidenediamine), which is the insecticidal compound used in Examples, is a compound having a melting point of 82.0° C. and a water-solubility of >590 g/L (at pH 7.0, 20° C.). Procymidone (N-(3,5-dichlorophenyl)-1,2-dimethylcyclopropane-1,2-dicarboximide), which is a fungicidal compound used in Examples, is a compound having a melting point of from 166 to 166.5° C. and a water-solubility of 4.5 mg/L (at 25° C.). Clothianidin ((E)-1-(2-chloro-1,3-thiazol-5-yl)-3-methyl-2-nitroguanidine) is a compound having a melting point of 176.8° C. and a water-solubility of 0.304 g/L (at pH 4.0, 20° C.).

Production Example 1

Two hundred grams of procymidone and 800 g of dihydroterpinel acetate (produced by Yasuhara Chemical Co., Ltd., content: 99.6%) were mixed, and the mixture was roughly pulverized for about 10 minutes using a high-speed shear stirrer (POLYTRON, manufactured by KINEMATICA AG). The resulting mixture was further subjected to wet-pulverization at a feeding rate of 3 L/hr and a peripheral speed of 10 m/sec using a DYNO-MILL (having a vessel size of 600 mL, manufactured by WILLY A. BACHOFEN AG. MASHINEN-FABRIK) filled with 1120 g of beads (1.25 mm zirconia). The procymidone particles after the wet pulverization had a volume median diameter of 2.2 μm. The procymidone particles were suspended almost uniformly in dihydroterpinel acetate and almost no flocculation was recognized. The suspension in the wet-pulverization had a viscosity of 2010 mPa·s (Brookfield viscometer, rotor No. 3, 6 rpm).

A mixture obtained by addition of 2.42 g of a polyisocyanate (Sumijule L-75, produced by Sumika Bayer Urethane Co., Ltd.) to 25 g of the resulting suspension was added to 39.2 g of deionized water in which 1.4 g of ethylene glycol and 3.29 g of gum arabic (Arabic Cole SS, produced by San-ei Yakuhin Boeki Co., Ltd.) had been dissolved therein and was stirred at 7000 rpm for 5 minutes using a Homogenizer (manufactured by Tokushu Kika Kogyo Co., Ltd.). The dispersion obtained had a viscosity of 2050 mPa·s (Brookfield viscometer, L-type rotor, 6 rpm).

The resulting dispersion was heated to 60° C. and was stirred at that temperature for 24 hours to yield an aqueous suspension composition containing procymidone microcapsules (henceforth, referred to as Aqueous Suspension Composition 1).

Production Example 2

Two hundred grams of nitempyram and 800 g of dihydroterpinel acetate (produced by Yasuhara Chemical Co., Ltd., content: 99.6%) were mixed, and the mixture was roughly pulverized for about 10 minutes using a high-speed shear stirrer (POLYTRON, manufactured by KINEMATICA AG). The resulting mixture was further subjected to wet-pulverization at a feeding rate of 3 L/hr and a peripheral speed of 10 m/sec using a DYNO-MILL (having a vessel size of 600 mL, manufactured by WILLY A. BACHOFEN AG. MASHINEN-FABRIK) filled with 1120 g of beads (1.25 mm zirconia). The suspension in the wet-pulverization had a viscosity of 2150 mPa·s (Brookfield viscometer, rotor No. 3, 6 rpm).

A mixture obtained by addition of 2.42 g of a polyisocyanate (Sumijule L-75, produced by Sumika Bayer Urethane Co., Ltd.) to 25 g of the resulting suspension was added to 39.2 g of deionized water in which 1.4 g of ethylene glycol and 3.29 g of gum arabic (Arabic Cole SS, produced by San-ei Yakuhin Boeki Co., Ltd.) had been dissolved therein and was stirred at 800 rpm for 5 minutes using a Homogenizer (manufactured by Tokushu Kika Kogyo Co., Ltd.).

The resulting dispersion was heated to 60° C. and was stirred at that temperature for 24 hours to yield an aqueous suspension composition containing nitempyram microcapsules (henceforth, referred to as Aqueous Suspension Composition 2).

Production Example 3

Two hundred grams of clothianidin and 800 g of dihydroterpinel acetate (produced by Yasuhara Chemical Co., Ltd., content: 99.6%) were mixed, and the mixture was roughly pulverized for about 10 minutes using a high-speed shear stirrer (POLYTRON, manufactured by KINEMATICA AG). The resulting mixture was further subjected to wet-pulverization at a feeding rate of 3 L/hr and a peripheral speed of 10 m/sec using a DYNO-MILL (having a vessel size of 600 mL, manufactured by WILLY A. BACHOFEN AG. MASHINENFABRIK) filled with 1120 g of beads (1.25 mm zirconia). The clothianidin particles after the wet pulverization had a volume median diameter of 2.6 μm. The clothianidin particles were suspended almost uniformly in dihydroterpinel acetate and almost no flocculation was recognized. The suspension in the wet-pulverization had a viscosity of 1400 mPa·s (Brookfield viscometer, rotor No. 2, 6 rpm, 25° C.).

A mixture obtained by addition of 2.42 g of a polyisocyanate (Sumijule L-75, produced by Sumika Bayer Urethane Co., Ltd.) to 25 g of the resulting suspension was added to 39.2 g of deionized water in which 1.42 g of ethylene glycol and 3.29 g of gum arabic (Arabic Cole SS, produced by San-ei Yakuhin Boeki Co., Ltd.) had been dissolved therein and was stirred at 7000 rpm for 5 minutes using a Homogenizer (manufactured by Tokushu Kika Kogyo Co., Ltd.). The dispersion obtained had a viscosity of 2050 mPa·s (Brookfield viscometer, L-type rotor, 6 rpm).

The resulting dispersion was heated to 60° C. and was stirred at that temperature for 24 hours to yield an aqueous suspension composition containing clothianidin microcapsules (henceforth, referred to as Aqueous Suspension Composition 3).

Production Example 4

A mixture obtained by addition of 5.47 g of a polyisocyanate (Sumijule L-75, produced by Sumika Bayer Urethane Co., Ltd.) to 25 g of the aqueous clothianidin suspension obtained in Production Example 3 was added to 44.5 g of deionized water in which 3.16 g of ethylene glycol and 3.29 g of gum arabic (Arabic Cole SS, produced by San-ei Yakuhin Boeki Co., Ltd.) had been dissolved therein and was stirred at 7000 rpm for 5 minutes using a Homogenizer (manufactured by Tokushu Kika Kogyo Co., Ltd.).

The resulting dispersion was heated to 60° C. and was stirred at that temperature for 24 hours to yield an aqueous suspension composition containing clothianidin microcapsules (henceforth, referred to as Aqueous Suspension Composition 4).

Comparative Production Example 1

An aqueous suspension composition containing microcapsules (henceforth, referred to as Comparative Suspension Composition 1) was obtained in the same manner as in Production Example 2, except for changing 800 g of dihydroterpinel acetate to 800 g of isodecyl adipate in Production Example 2. However, when the resulting microcapsules were observed by using an optical microscope, presence of no solid particles was recognized in the microcapsules.

Comparative Production Example 2

An aqueous suspension composition containing microcapsules (henceforth, referred to as Comparative Suspension Composition 2) was obtained in the same manner as in Production Example 4, except for changing 800 g of dihydroterpinel acetate to 800 g of isodecyl adipate in Production Example 4. However, when the resulting microcapsules were observed by using an optical microscope, presence of no solid particles was recognized in the microcapsules.

Test Example 1

Storage Stability at High Temperature

The aqueous suspension compositions of microcapsules obtained in Production Examples 1, 2 and 3 were stored at 54° C. for 2 weeks. The conditions of microcapsules in the aqueous suspension compositions before and after the storage were observed by the following method.

After shaking each aqueous suspension composition of microcapsules well 20 times, 20 μL of each composition was measured out precisely and was diluted with 2 mL of distilled water. For each diluted liquid, one drop thereof was put on a slideglass and the number of microcapsules present in a 372 μm×500 μm visual field was counted using an optical microscope (HI-SCOPE Advanced KH-3000 manufactured by HIROX) at a magnification of ×350. The counting of the number of microcapsules in each sample was conducted at three different visual fields for a sample on one slideglass and the average of the measurements was considered as a microcapsule density. The results are listed in Table 1.

TABLE 1

| | Microcapsule density in visual field | |
|---|---|---|
| | Just after production | After storage at 54° C. for 2 weeks |
| Aqueous Suspension Composition 1 | 13 | 14 |
| Aqueous Suspension Composition 2 | 18 | 16 |
| Aqueous Suspension Composition 3 | 70 | 70 |

No change was recognized in the conditions of the microcapsules observed and no noticeable change in the number of the microcapsules in a visual field was also found.

Test Example 2

Microencapsulation Ratio

For each of the aqueous suspension compositions of microcapsules obtained in Production Examples 3, 4 and Comparative Production Example 2, 10 g of the composition was sampled and was centrifuged (HIMAC SCR20BB, manufactured by HITACHI, Ltd., centrifugal rotor used: PRP-20) at 10000 rpm for 30 minutes. Then, the content of clothianidin in the supernatant of each sample was measured and the amount of clothianidin distributed outside the coating film of a microcapsule was determined. Then, the microencapsulation ratio of clothianidin was calculated. The results are shown in Table 2.

In addition, the amount of clothianidin within a microcapsule after the storage of the microcapsule aqueous suspension composition at 54° C. for 2 weeks was also measured and the result is also shown in Table 2.

TABLE 2

| | Content of clothianidin in microcapsule (just after production) | Content of clothianidin in microcapsule (after 2 weeks at 54° C.) |
|---|---|---|
| Aqueous Suspension Composition 3 | 99.2 | 99.3 |
| Aqueous Suspension Composition 4 | 99.2 | 99.1 |
| Comparative Suspension Composition 2 | 0< | |

INDUSTRIAL APPLICABILITY

The microcapsule of the present invention is useful to a sustained-release formulation of pesticidal compounds.

The invention claimed is:

1. A microcapsule comprising a liquid droplet, wherein the liquid droplet comprises a solid pesticidal compound suspended in terpineol, dihydroterpineol, terpinel acetate, dihydroterpinel acetate or a mixture thereof, and wherein the liquid droplet is coated with a resin.

2. The microcapsule according to claim 1, wherein the solid pesticidal compound is suspended in dihydroterpinel acetate.

3. The microcapsule according to claim 1, wherein the solid pesticidal compound is a neonicotinoid compound.

4. The microcapsule according to claim 1, wherein the solid pesticidal compound is clothianidin.

5. The microcapsule according to claim 1, wherein the solid pesticidal compound is nitenpyram.

6. The microcapsule according to claim 1, wherein the solid pesticidal compound is procymidone.

7. The microcapsule according to any one of claims 1 to 6, wherein the resin is a polyurethane resin or a polyurea resin.

8. The microcapsule according to claim 7, wherein the microcapsule has a volume median diameter within the range of from 5 to 50 µm.

9. A method for producing a microcapsule comprising (a) pulverizing a solid pesticidal compound in terpineol, dihydroterpineol, terpinel acetate, dihydroterpinel acetate or a mixture thereof to form a suspension, (b) mixing the resulting suspension and water to prepare a liquid droplet, and (c) forming a coating film of a resin around the liquid droplet.

10. The method for producing a microcapsule according to claim 9, wherein the resin is a polyurethane resin or a polyurea resin.

* * * * *